US00PP22115P2

(12) United States Plant Patent
MacKenzie

(10) Patent No.: US PP22,115 P2
(45) Date of Patent: Sep. 6, 2011

(54) ***ALLIUM* PLANT NAMED 'NONEUQ'**

(50) Latin Name: *Allium tanguticum*
Varietal Denomination: Noneuq

(75) Inventor: David MacKenzie, Nunica, MI (US)

(73) Assignee: Hortech, Inc., Springlake, MI (US)

( * ) Notice: Subject to any disclaimer, the term of this patent is extended or adjusted under 35 U.S.C. 154(b) by 71 days.

(21) Appl. No.: 12/658,195

(22) Filed: Feb. 4, 2010

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — Kent L Bell
(74) *Attorney, Agent, or Firm* — Penny J. Aguirre

(57) ABSTRACT

A new cultivar of *Allium* plant named 'Noneuq' characterized by its compact habit, its strap-like glossy leaves, and its umbels of numerous dark purple-pink flowers.

2 Drawing Sheets

Botanical classification: *Allium tanguticum.*
Variety denomination: 'Noneuq'.

BACKGROUND OF THE INVENTION

The present invention relates to a new and distinct cultivar of *Allium* plant, botanically known as *Allium tanguticum* 'Noneuq' and will be referred to hereinafter by its cultivar name, 'Noneuq'. The new cultivar of *Allium* is a hardy herbaceous perennial grown for use as a landscape and container plant.

'Noneuq' was discovered in summer 2005 as a naturally occurring whole plant mutation of *Allium tanguticum* 'Summer Beauty' (not patented) in the Inventor's trial garden in Nunica, Mich. *Allium tanguticum* is also listed by the synonym *Allium senescens* subsp. *montanum*, however 'Summer Beauty' is most commonly listed in commerce as a cultivar of *Allium tanguticum.*

Asexual reproduction of the new cultivar was first accomplished by bulb division in Nunica, Mich. in July of 2005. Propagation has determined the characteristics to be stable and reproduced true to type in successive generations.

SUMMARY OF THE INVENTION

The following traits have been repeatedly observed and are determined to be the characteristics of the new cultivar. These attributes in combination distinguish 'Noneuq' as a unique cultivar of *Allium.*

1. 'Noneuq' exhibits umbels of numerous flowers that are dark purple-pink in color.
2. 'Noneuq' exhibits a compact, short habit due to its leaves that are short in length, reaching an average of 9 inches in length.
3. 'Noneuq' exhibits leaves that are strap-like with a glossy appearance.

'Noneuq' can be most closely compared to its parent, 'Summer Beauty'. 'Summer Beauty' differs from 'Noneuq' in having longer leaves, a less compact and taller plant height, a lower number of flowers per umbel and in having flowers that are lighter lavender-pink in color. 'Noneuq' can also be compared to the cultivar 'Blue Skies' (not patented). 'Blue Skies' differs from 'Noneuq' in being taller in height with longer leaves, in having a less compact habit, and in having flowers that are lighter lavender-pink in color.

BRIEF DESCRIPTION OF THE DRAWINGS

The accompanying colored photographs illustrate the overall appearance and distinct characteristics of the new *Allium*. The photographs were taken in July of 2 year-old plants of 'Noneuq' as grown in a trial bed in full sun in Nunica, Mich.

The photograph in FIG. 1 provides a view of 'Noneuq' in bloom and illustrates its compact plant habit.

Figure 1:
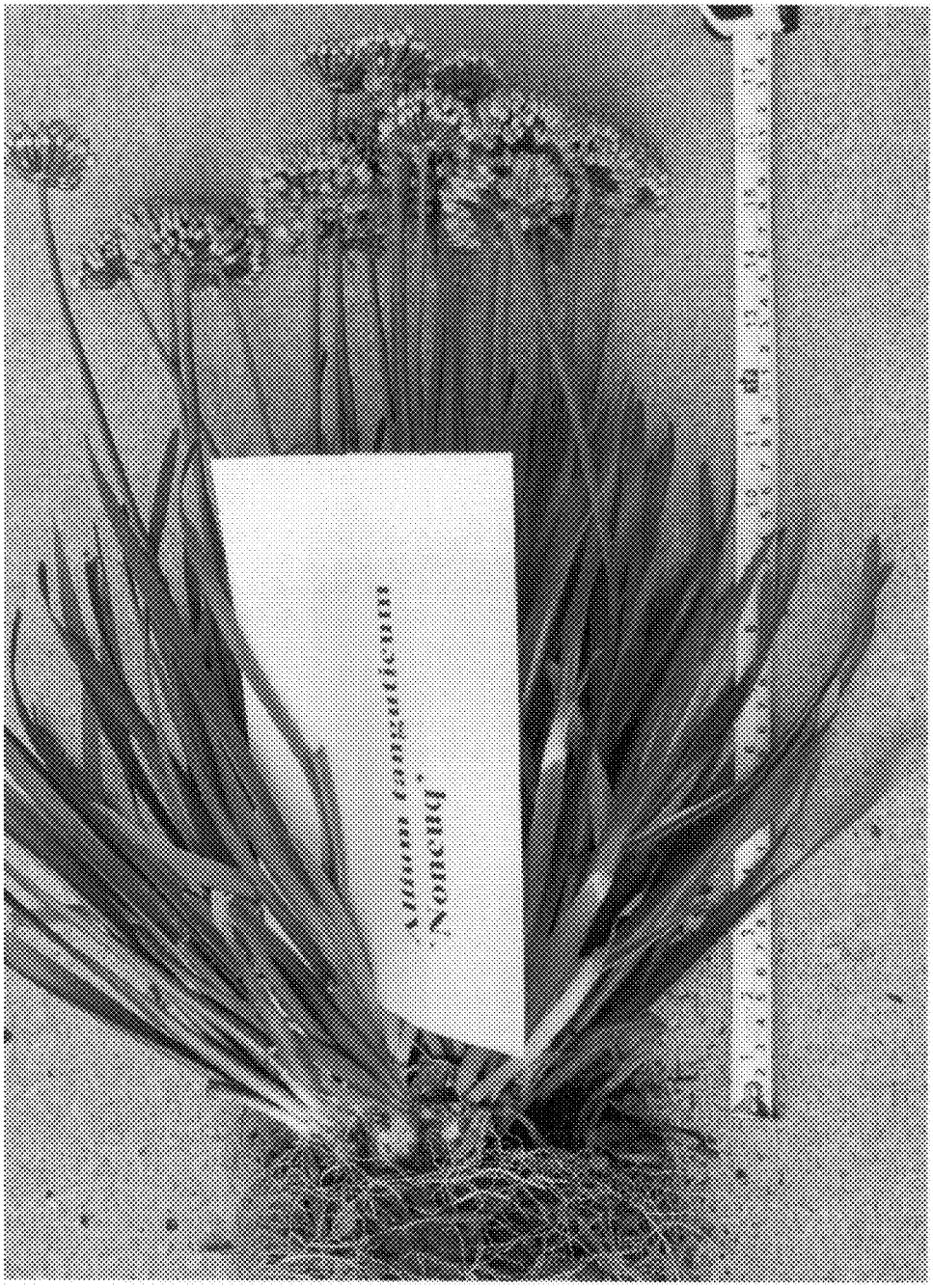
Figure 2:
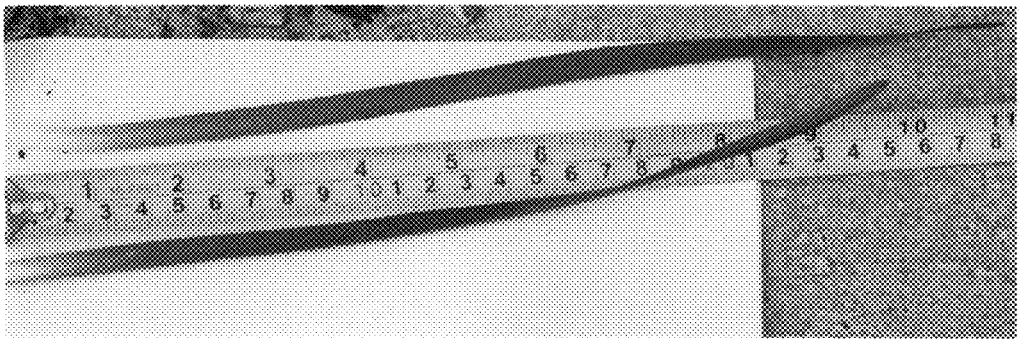

The photograph in FIG. 2 provides a close-up view of 2 leaves of 'Noneuq'.

Figure 3:
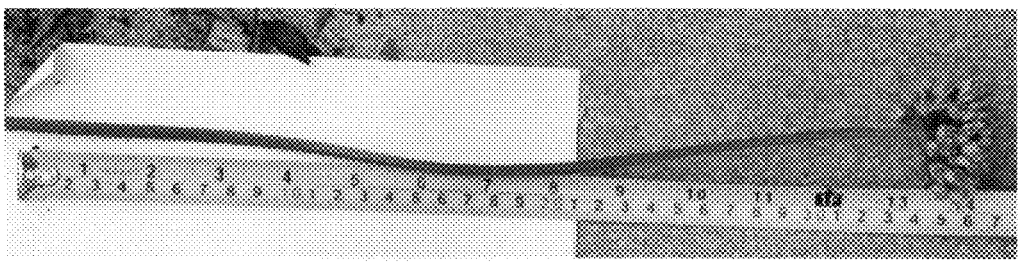

The photograph in FIG. 3 provides a view of a single flowering stem of 'Noneuq'.

Figure 4:
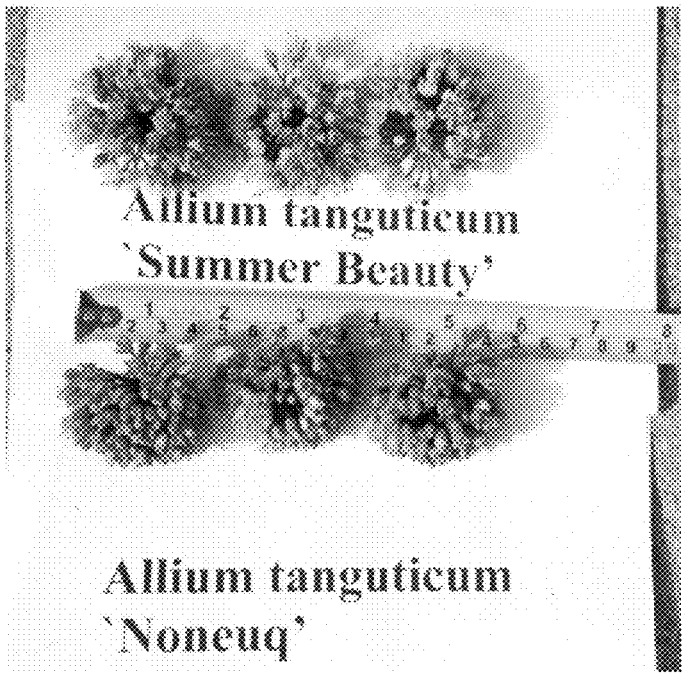

The photograph in FIG. 4 provides a view of inflorescences of 'Noneuq' on the bottom and inflorescences of the parent, 'Summer Beauty' on the top.

The colors in the photographs may differ slightly from the color values cited in the detailed botanical description, which accurately describe the colors of the new *Allium.*

DETAILED BOTANICAL DESCRIPTION

The following is a detailed description of the new cultivar as observed on 2 year-old plants of 'Noneuq' as grown in a trial bed in full sun in Nunica, Mich. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

General description:

*Blooming habit.*—June to July in Michigan.

*Plant habit.*—Herbaceous, perennial bulb with a tightly clump forming, compact and vase-shaped habit.

*Height and spread.*—An average of 18 to 24 inches in height in bloom with foliage an average of 15 cm in height, reaches a spread of about 24 inches.

*Hardiness.*—At least in U.S.D.A. Zones 4b to 8b.

*Diseases and pests.*—No unique aspects concerning susceptibility or resistance to diseases or pests has been observed.

*Root description.*—Fibrous from base of bulbs.

*Branching.*—Stem-less, tufted shoots arise from bulbs.

*Bulb description.*—Oval-conical in shape, an average of 1½ inches in length and 1¼ inches in width, 155A in color and covered with dried foliage 165C in color.

Growth and propagation:

*Propagation.*—Bulb division.

*Growth rate.*—Vigorous.

Foliage description:

*Leaf shape.*—Linear.

*Leaf division.*—Simple.

*Leaf base.*—Truncate to bulb.

*Leaf apex.*—Acute.

*Leaf aspect.*—Primarily upright.

*Leaf venation.*—Parallel, not prominent or conspicuous, color matches leaf color.

*Leaf margins.*—Entire.

*Leaf fragrance.*—Onion scented.

*Leaf attachment and arrangement.*—Sessile, arise in tufts from bulb.

*Leaf substance.*—Semi-succulent.

*Leaf size.*—¼ to ⅜ inch in width and 8 to 10 inches in length when mature.

*Leaf surface.*—Glabrous and shiny on upper and lower surface.

*Leaf color.*—141B (Upper and Lower surfaces, immature and mature).

Flower description:

*Inflorescence type.*—Terminal umbel.

*Lastingness of inflorescence.*—About one month.

*Inflorescence size.*—An average of 1 inch in depth and 2 inches in diameter.

*Flower fragrance.*—Onion scented.

*Flower number.*—Average of 60 per inflorescence, one inflorescence per stem, 20 to 30 per plant.

*Flower aspect.*—Upright to outward, dependant on location of the inflorescence.

*Flower bud.*—An average of ¼ inch in length and 3/16 inches in width, conical in shape, 75A in color.

*Flower form.*—Campanulate.

*Flower size.*—An average of ¼ inch in length and width.

*Tepals.*—6, ovate in shape, about ¼ inch in length and 3/16 inch in width, apex acute, base rounded, entire margins, when opening and mature, upper and lower surface; 83B in color in center blending to edges 76A, surface is glabrous on upper and lower surface.

*Peduncles* (*flower stem*).—Oval in shape, strong, an average of 13 inches in length and ⅛ inch in width, primary held upright, glabrous surface, 141B in color.

*Pedicels.*—Oval in shape, an average of ¼ inch in length and 1/32 inch in width, glabrous surface, 141C in color, surface glabrous.Reproductive Organs:

*Gynoecium.*—3 pistils, ⅛ inch in length, stigmas broad, 1.8 inch in width and 75A in color, styles ⅛ inch in length and 75A in color, ovary ⅛ inch in diameter and 155A in color.

*Androcoecium.*—5 stamens, ¼ to ⅜ inch in length, filaments are 1/32 inch in width and 75B in color, pollen is moderate in quantity and 12A in color.

*Fruit.*—Rounded aggregate fruit, 202A in color, an average of 3/16 inch in height and width.

It is claimed:

1. A new and distinct variety of *Allium* plant named 'Noneuq' as described and illustrated herein.

* * * * *